United States Patent
Salamon et al.

(10) Patent No.: US 7,420,682 B2
(45) Date of Patent: Sep. 2, 2008

(54) SENSOR DEVICE FOR INTERFERENCE AND PLASMON-WAVEGUIDE/INTERFERENCE SPECTROSCOPY

(75) Inventors: Zdzislaw Salamon, Tucson, AZ (US); Gordon Tollin, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 386 days.

(21) Appl. No.: 10/571,381

(22) PCT Filed: Sep. 30, 2003

(86) PCT No.: PCT/US03/30694

§ 371 (c)(1),
(2), (4) Date: Mar. 10, 2006

(87) PCT Pub. No.: WO2005/040760

PCT Pub. Date: May 6, 2005

(65) Prior Publication Data

US 2007/0030489 A1    Feb. 8, 2007

(51) Int. Cl.
G01N 21/55   (2006.01)

(52) U.S. Cl. .................. 356/445; 356/517; 356/448

(58) Field of Classification Search ......... 356/445–448, 356/244, 128, 135, 517
See application file for complete search history.

(56) References Cited

U.S. PATENT DOCUMENTS

| | | | |
|---|---|---|---|
| 5,327,225 A | 7/1994 | Bender et al. | |
| 5,344,784 A | 9/1994 | Attridge | |
| 5,846,843 A | 12/1998 | Simon | |
| 6,421,128 B1 | 7/2002 | Salamon et al. | |
| 6,628,376 B1 | 9/2003 | Nikitin et al. | |
| 6,970,249 B1 * | 11/2005 | Lipson et al. | 356/445 |

* cited by examiner

Primary Examiner—L. G Lauchman
(74) Attorney, Agent, or Firm—Gavin J. Milczarek-Desai; Quarles & Brady LLP (57) ABSTRACT

Methods for measuring a property of a sample material present at an interface of an emerging medium in a spectroscopic device include a sensor (10) featuring at least one dielectric member (14) disposed upon a entrant medium (12), with the dielectric member being of an optical thickness selected to produce an observable interference effect for an incident angle of light below the critical angle of total internal reflection at the interface with the dielectric member (14). The dielectric member (14) of the sensor device (10) may be modified and functionalized for binding of a sample analyte by disposing a sensing surface area (38, 40, 42) upon it. Moreover, an metal layer (18) may be added to an entrant medium (20) to produce a sensor (16) that generates observable optical phenomena both above (resonance) and below (interference) a given critical angle.

28 Claims, 12 Drawing Sheets

SENSOR DEVICE FOR INTERFERENCE AND PLASMON-WAVEGUIDE/INTERFERENCE SPECTROSCOPY

U.S. GOVERNMENT RIGHTS

This invention was made with Federal Government support under Contract Number MCB-9904753 awarded by the National Science Foundation and Contract Number GM-59630 awarded by the National Institutes of Health. The Government has certain rights in the invention.

CROSS-REFERENCE TO RELATED APPLICATIONS

This application claims benefit of priority under 35 U.S.C. 119(e) to International Application No. PCT/US03/30694 filed on Sep. 30, 2003, the entire contents of which are incorporated herein by reference.

BACKGROUND OF THE INVENTION

1. Field of the Invention

This invention relates in general to optical sensor chips and more particularly to an optical sensor chip that utilizes the phenomenon of optical interference to spectroscopically characterize the properties of molecules below the critical angle of incidence.

2. Description of the Related Art

Surface plasmon resonance is a phenomenon used in many analytical applications in metallurgy, microscopy, and chemical and biochemical sensing. Along with optical techniques such as ellipsometry, multiple internal reflection spectroscopy, and differential reflectivity, SPR is one of the most sensitive techniques to surface and interface effects. This inherent property makes SPR well suited for nondestructive studies of surfaces, interfaces, and very thin layers. The SPR phenomenon has been known for decades and the theory is fairly well developed. Simply stated, a surface plasmon is an oscillation of free electrons that propagates along the surface of a conductor. The phenomenon of surface plasmon resonance occurs under total internal reflection conditions at the boundary between substances of different refractive indices, such as glass and water solutions. When an incident light beam is reflected internally within the first medium, its electromagnetic field produces an evanescent wave that crosses a short distance (in the order of nanometers) beyond the interface with the second medium. If a thin metal film is inserted at the interface between the two media, surface plasmon resonance occurs when the free electron clouds in the metal layer (the plasmons) absorb energy from the evanescent wave and cause a measurable drop in the intensity of the reflected light at a particular angle of incidence that depends on the refractive index of the second medium.

Typically, the conductor used for SPR spectrometry is a thin film of metal such as silver or gold; however, surface plasmons have also been excited on semiconductors. The conventional method of exciting surface plasmons is to couple the transverse-magnetic (TM) polarized energy contained in an evanescent field to the plasmon mode on a metal film. The amount of coupling, and thus the intensity of the plasmon, is determined by the incident angle of the light beam and is directly affected by the refractive indices of the materials on both sides of the metal film. By including the sample material to be measured as a layer on one side of the metallic film, changes in the refractive index of the sample material can be monitored by measuring changes in the surface plasmon coupling efficiency in the evanescent field. When changes occur in the refractive index of the sample material, the propagation of the evanescent wave and the angle of incidence producing resonance are affected. Therefore, by monitoring the angle of incidence at a given wavelength and identifying changes in the angle that causes resonance, corresponding changes in the refractive index and related properties of the material can be readily detected.

As those skilled in the field readily understand, total reflection can only occur above a particular critical incidence angle if the refractive index of the incident or entrant medium (typically a prism or grating) is greater than that of the emerging medium. In practice, total reflection is observed only for incidence angles within a range narrower than from the critical angle to 90 degrees because of the physical limitations inherent with the testing apparatus. Similarly, for systems operating with variable wavelengths and a given incidence angle, total reflection is also observed only for a corresponding range of wavelengths. This range of incidence angles (or wavelengths) is referred to as the "observable range" for the purpose of this disclosure. Moreover, a metal film with a very small refractive index (as small as possible) and a very large extinction coefficient (as large as possible) is required to support plasmon resonance. Accordingly, gold and silver are appropriate materials for the thin metal films used in visible-light SPR; in addition, they are very desirable because of their mechanical and chemical resistance.

Thus, once materials are selected for the prism, metal film and emerging medium that satisfy the described conditions for total reflection and plasmon resonance, the reflection of a monochromatic incident beam becomes a function of its angle of incidence and of the metal's refractive index, extinction coefficient, and thickness. The thickness of the film is therefore selected such that it produces observable plasmon resonance when the monochromatic light is incident at an angle within the observable range.

The classical embodiments of SPR devices are the Kretschmann and Otto prism or grating arrangements, which consist of a prism with a high refractive index n (in the 1.4-1.7 range) coated on one face with a thin film of metal. The Otto device also includes a very thin air gap between the face of the prism and the metal film. In fact, the gap between the prism (or grating) and the metal layer, which is in the order of nanometers, could be of a material other than air, even metal, so long as compatible with the production of observable plasmon resonance in the metal film when the monochromatic light is incident at an angle within the observable range.

Similar prior SPR devices are based on the phenomenon of long-range surface plasmon resonance, which is also generated with p-polarized light using a dielectric medium sandwiched between the incident medium and a thinner metal layer (than in conventional SPR applications). The metal film must be sufficiently thin and the dielectric and emergent media must be beyond the critical angle (i.e., having refractive indices smaller than the refractive index of the entrant medium) so that they support evanescent waves to permit the simultaneous coupling of surface plasmons at the top and bottom interfaces of the thin metal layer (i.e., to permit excitation of surface waves on both sides of the thin metal film). This condition is necessary in order for the phenomenon of long-range surface plasmon resonance to occur. For a given set of parameters, the distinguishing structural characteristic between conventional surface plasmon resonance and long-range surface plasmon resonance is the thickness of the metal film and of the inner dielectric film (the latter not being necessary for conventional SPR). In the conventional technique, the metal film must be sufficiently thick and must be placed either directly on the entrant medium (i.e., prism or grating) or on a dielectric film which is too thin to allow excitation of the surface bound waves on both metal surfaces, to produce observable plasmon resonance when a monochromatic light is incident at an angle within the observable range.

In long-range surface plasmon resonance (LRSPR), in contrast, the metal film must be placed between two dielectric media that are beyond the critical angle so that they support evanescent waves, and must be thin enough to permit excitation of surface waves on both sides of the metal film. The specific thickness depends on the optical parameters of the various components of the sensor in question, but film thicknesses in the order of 45-55 nm for gold and silver are recognized as critical for conventional SPR, while no more than about half as much (15-28 nm) can be used for LRSPR. It is noted that the thickness required to support either form of surface plasmon resonance for a specific system can be calculated by one skilled in the art on the basis of the system's optical parameters.

As well understood by those skilled in the art, the main criterion for a material to support SP waves is that it have a negative real dielectric component, which results from the refractive and extinction properties mentioned above for the metal layer. The surface of the metal film forms the transduction mechanism for the SPR device and is brought into contact with the sample material to be sensed at the interface between the metal film and the emerging medium contained in a cell assembly. Monochromatic light is emitted by a laser or equivalent light source into the prism or grating and reflected off the metal film to an optical photodetector to create the sensor output. The light launched into the prism and coupled into the SP mode on the film is p-polarized with respect to the metal surface where the reflection takes place. In all these prior-art devices and techniques, only p-polarized light is coupled into the plasmon mode because this particular polarization has the electric field vector oscillating normal to the plane that contains the metal film. This is sometimes referred to as transverse-magnetic (TM) polarization.

As mentioned, the surface plasmon is affected by changes in the dielectric value of the material in contact with the metal film. As this value changes, the conditions necessary to couple light into the plasmon mode also change. Thus, SPR is used as a highly sensitive technique for investigating changes that occur at the surface of the metal film. In particular, over the last several years there has been a keen interest in the application of surface plasmon resonance spectroscopy to study the optical properties of molecules immobilized at the interface between solid and liquid phases.

The ability of the SPR phenomenon to provide information about the physical properties of dielectric thin films deposited on a metal layer, including lipid and protein molecules forming proteolipid membranes, is based upon two principal characteristics of the SPR effect. The first is the fact that the evanescent electromagnetic field generated by the free electron oscillations decays exponentially with penetration distance into the emergent dielectric medium; i.e., the depth of penetration into the material in contact with a metal layer extends only to a fraction of the light wavelength used to generate the plasmons. This makes the phenomenon sensitive to the optical properties of the metal/dielectric interface without any interference from the properties of the bulk volume of the dielectric material or any medium that is in contact with it. The second characteristic is the fact that the angular (or wavelength) position and shape of the resonance curve is very sensitive to the optical properties of both the metal film and the emergent dielectric medium adjacent to the metal surface. As a consequence of these characteristics, SPR is ideally suited for studying both structural and mass changes of thin dielectric films, including lipid membranes, lipid-membrane/protein interactions, and interactions between integral membrane proteins and peripheral, water-soluble proteins. See Salamon, Z., H. A. Macleod and G. Tollin, "Surface Plasmon Resonance Spectroscopy as a Tool for Investigating the Biochemical and Biophysical Properties of Membrane Protein Systems. I: Theoretical Principles," *Biochim. et Biophys. Acta,* 1331: 117-129 (1997); and Salamon, Z., H. A. Macleod and G. Tollin, "Surface Plasmon Resonance Spectroscopy as a Tool for Investigating the Biochemical and Biophysical Properties of Membrane Protein Systems. II: Applications to Biological Systems," *Biochim. et Biophys. Acta,* 1331: 131-152 (1997).

In U.S. Pat. No. 5,991,488, herein incorporated by reference, we disclosed new thin-film interface designs that couple surface plasmon and waveguide excitation modes. The technique, defined as coupled plasmon-waveguide resonance (CPWR), is based on the concept of coupling plasmon resonances in a thin metal film with the waveguide modes in a dielectric overcoating. Accordingly, a metallic layer, typically either gold or silver, is used with a prism so as to provide a surface plasmon wave by conventional SPR (or waves by long-range SPR) and is further covered with a solid dielectric layer characterized by predetermined optical parameters. The dielectric member inserted between the metal film and the emergent medium is selected such that coupled plasmon-waveguide resonance effects are produced within an observable range.

The emergent dielectric medium is then placed in contact with this solid dielectric layer. As disclosed in the patent, we found that the additional layer of dielectric material functions as an optical amplifier that produces an increased sensitivity and enhanced spectroscopic capabilities in SPR. In particular, the added dielectric layer makes it possible to produce resonance with either s- or p-polarized light. In addition, the added dielectric protects the metal layer and could be used as a matrix for adsorbing and immobilizing the sensing materials in CPWR-based biosensor applications, as disclosed in PCT Application Serial No. US03/0273, which is herein incorporated by reference.

Nonetheless, a remaining drawback of SPR and CPWR is that one is limited to measuring resonance effects above the critical angle for total internal reflectance. In other words, conventional SPR and CPWR are limited to the probing of optical properties observable in the reflectance mode of a spectrometer. Moreover, conventional CPWR sensors contain a dielectric layer or member that is on the order of nanometers in thickness, which can be too thin and fragile for certain surface modifications (e.g., etching techniques) and thus limit the versatility of the sensor.

Therefore, a need still exists for a new and useful sensor chip that overcomes some of the problems and shortcomings of the art.

SUMMARY OF THE INVENTION

The invention relates in general to a new sensor device that utilizes optical interference for measuring properties of molecules and/or thin films at surfaces and interfaces. More specifically, the sensor device of invention is able to probe the optical properties of surfaces and interfaces both in the reflectance and transmittance modes by utilizing a dielectric layer or member of appropriate optical thickness to generate interference effects that are observable below the critical angle of total internal refection. This is in contrast with conventional SPR and CPWR spectroscopy, which are essentially limited to measurements of resonance effects above the critical angle. Moreover, a metal or semiconductor layer can be added to the sensor of the invention such that both interference effects and coupled-plasmon waveguide resonance effects can be measured for a given analyte.

In a preferred embodiment, the sensor device includes an entrant medium in optical contact with a dielectric member (e.g., $SiO_2$) that is about 100 microns in thickness. A sample solution is placed on the dielectric member and an incident angle of light below the critical angle for total internal reflection is reflected by and transmitted through the dielectric member, thereby producing observable interference effects in both reflectance and transmittance modes.

In another preferred embodiment, the device includes an entrant medium and a metal (or semiconductor) layer or layers with appropriate optical parameters and thickness (e.g., gold or silver with a thickness between 25-85 nm) in which surface plasmons can be generated by light. A dielectric member is in optical contact with the metal layer and functions both as a plasmon waveguide and as an optical interference system. Thus, especially sensitive spectroscopy can be performed because either optical interference effects or plasmon-waveguide resonance effects (or both) can be measured at incident angles of light both below and above the critical angle.

One of the main goals of this invention is the development of sensor devices that expand the observable range of optical phenomena that can be used to characterize molecules during spectroscopy. To that end, the invention further relates to a sensor unit for use in a system based on CPWR technology that includes a dielectric substrate having one or more sensing areas that contain at least one functional group supporting bi- or polyfunctional molecules capable of specific binding with molecules present in a sample analyte. Preferably, coupling between the bi- or polyfunctional molecules and the molecule(s) in the sample is selectively reversible such that the bi- or polyfunctional molecule-functionalized sensing areas can be regenerated, permitting repeated use of the functionalized sensor unit.

The sensor of the present invention differs from previous SPR and CPWR sensors in several key respects. First, the invention features a dielectric member that is approximately an order of magnitude thicker than that found on previous sensors (i.e., 10-1000 microns thick as opposed to 50-1200 nanometers). The inventors discovered that a dielectric material of an appropriate optical thickness (defined in the art as the product of refractive index and geometric thickness of the dielectric medium) can be used to generate optical interference effects, which can be measured in transmittance or reflectance modes at incident angles of light below the critical angle during spectroscopy. Second, CPWR sensors are limited to either p- or s-polarized light because plasmon oscillations occur only in the p and s directions; sensors of the present invention are not so limited. Third, the thick dielectric member allows many forms of surface modification to be practiced with less risk of damage to the sensor. Fourth, when a metal or semiconductor layer is added to the interference-causing dielectric layer of the present invention, the resulting sensor produces observable spectra at any angle of incidence (i.e., interference effects below the critical angle and coupled-plasmon waveguide resonance effects above the critical angle for total internal reflection).

Thus, an objective of the invention is to provide a sensor for investigating the properties of molecules at surfaces and interfaces that is capable of generating observable interference effects.

Another object of the invention is to provide a sensor device that generates observable spectral effects below the critical angle of total internal reflection for a given interface.

Another goal of the invention is to provide a method for measuring a property of a sample material present at an interface of an emerging medium that utilizes transmitted light in addition to reflected light.

Another important objective is to provide a sensor that is suitable for testing samples using monochromatic light with an angle of incidence ranging from 0 to 90 degrees.

Yet another goal of the invention is to provide a technique that makes it possible to achieve high throughput testing applications with an efficient, practical and economically feasible implementation.

Still another objective is to provide sensor devices that are suitable for direct incorporation with existing CPWR spectroscopic and other spectroscopic instruments.

Therefore, according to these and other objectives, the present invention pertains to novel and improved sensors featuring dielectric members of appropriate optical thickness such that observable optical interference effects can be measured during spectroscopy.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS

This invention is the result of further development of the CPWR devices described in our previous U.S. Pat. Nos. 6,421,128; 6,330,387; 5,991,488. In general the invention relates to a sensor for measuring the properties of molecules at surfaces and interfaces that has a dielectric layer or member that is of an optical thickness selected to produce an observable interference effect for an incident angle of light below a critical angle of total internal reflection. Moreover, the invention involves a sensor that combines the phenomena of optical interference and coupling of plasmons into waveguide modes in one sensing device. Thus, the sensor of the invention may be used to measure observable effects that occur both above and below the critical angle for total internal reflection.

It should be understood that the dielectric layer of the invention is in addition to and separate from the sample material or analyte with which the invention is used. The sample material at the interface with the emerging medium is often itself dielectric in nature, but its properties cannot be used to obtain the advantages of the invention without the addition of a appropriate dielectric layer as disclosed in this application. Therefore, all references to dielectric material pertain only to the additional layer contemplated herein.

Figure 1:
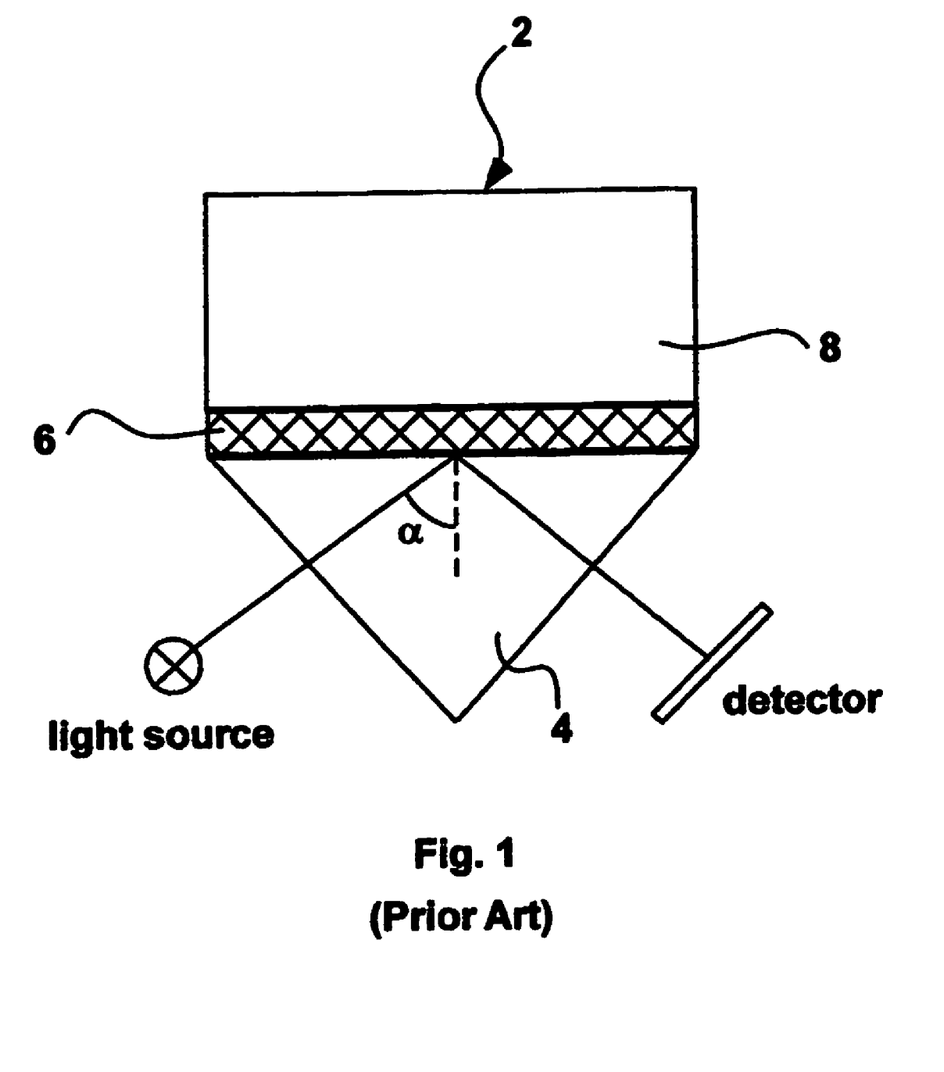
FIG. 1 is a schematic view of a coupled plasmon-waveguide resonance spectroscopic tool according to the prior art in an attenuated total reflection measuring system, wherein a glass prism coated with a 50 nm-thick silver layer is protected by a 460 nm-thick $Sio_2$ film.

Turning to FIG. 1, a CPWR sensor device 2 of the prior art is illustrated schematically. An entrant medium 4 (in this case, a prism) is coated with a metal layer 6 such as silver or gold about 50 nm in thickness. The metal layer 6 produces plasmons in response to light waves generated by the light source at an incident angle $\alpha$. A 460 nm coating of dielectric material 8 (such as glass) acts as a plasmon waveguide such that resonance effects can be measured when s- and p-polarized light is used. However, resonance effects are limited to conditions at which the incident angle of light is above the critical angle for total internal refection.

Figure 2:
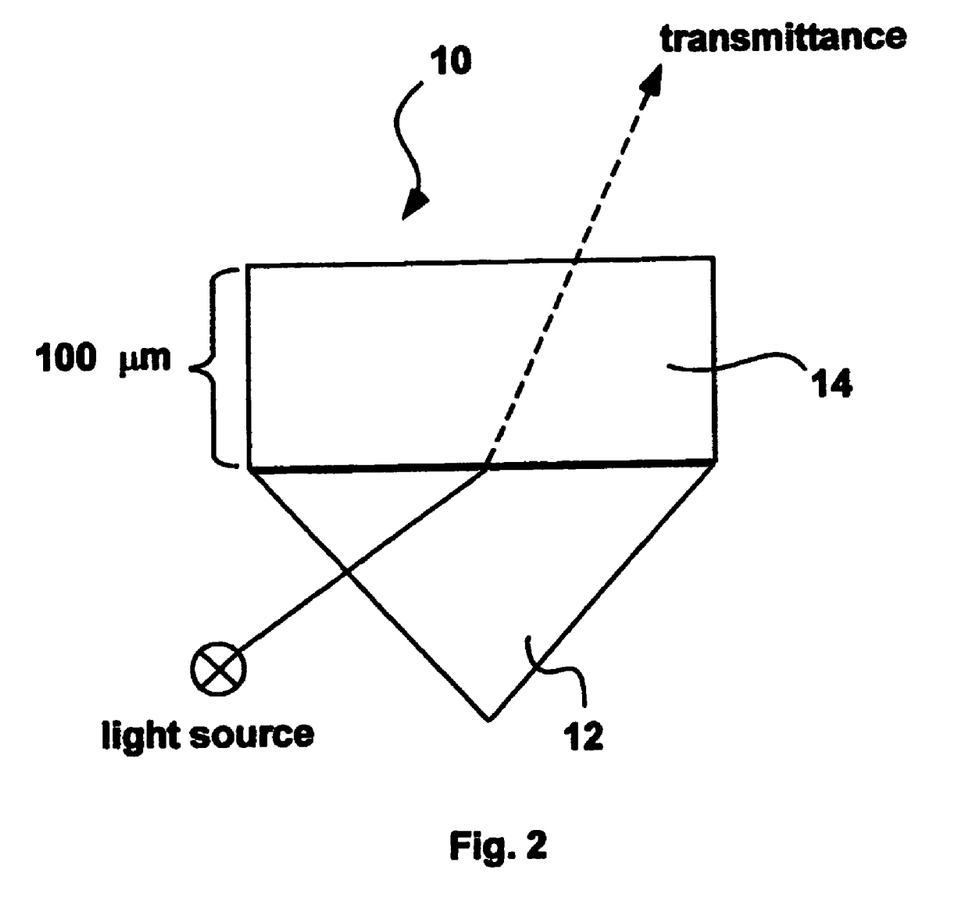
FIG. 2 is a schematic view of a preferred embodiment of the sensor of the invention.

FIG. 2 shows an embodiment of the invention in which a sensor 10 includes an entrant medium 12 in optical contact with a dielectric member 14 that is about 100 micrometers in thickness. Because interference effects are visible at incident angles below the critical angle for total internal reflection, changes in surface properties can be measured. Thus, optical interference effects both in transmittance or reflectance are used to characterize a property of a sample placed upon the dielectric member 14.

Suitable dielectric materials must be selected to provide an optical thickness that will produce an observable interference effect for an incident angle of light below the critical angle of total internal reflection. For example, a glass prism coated with a 100 micrometer-thick $SiO_2$ layer ($n_d$=1.4571, $k_d$=0.0030) is suitable to practice the invention with an aqueous analyte ($n_e$=1.33). Other possible dielectric materials included, but are not limited to, $TiO_2$, $MgF_2$, $AL_2O_3$, $LaF_3$, $Na_3ALF_6$, $ZnS$, $ZiO_2$, $Y_2O_3$, $HfO_3$, $Ta_2O_5$, ITO, nitrites or oxy-nitrites of silicone and aluminum, and combinations of these (e.g., layers of $TiO_2$ and $SiO_2$).

Figure 3:
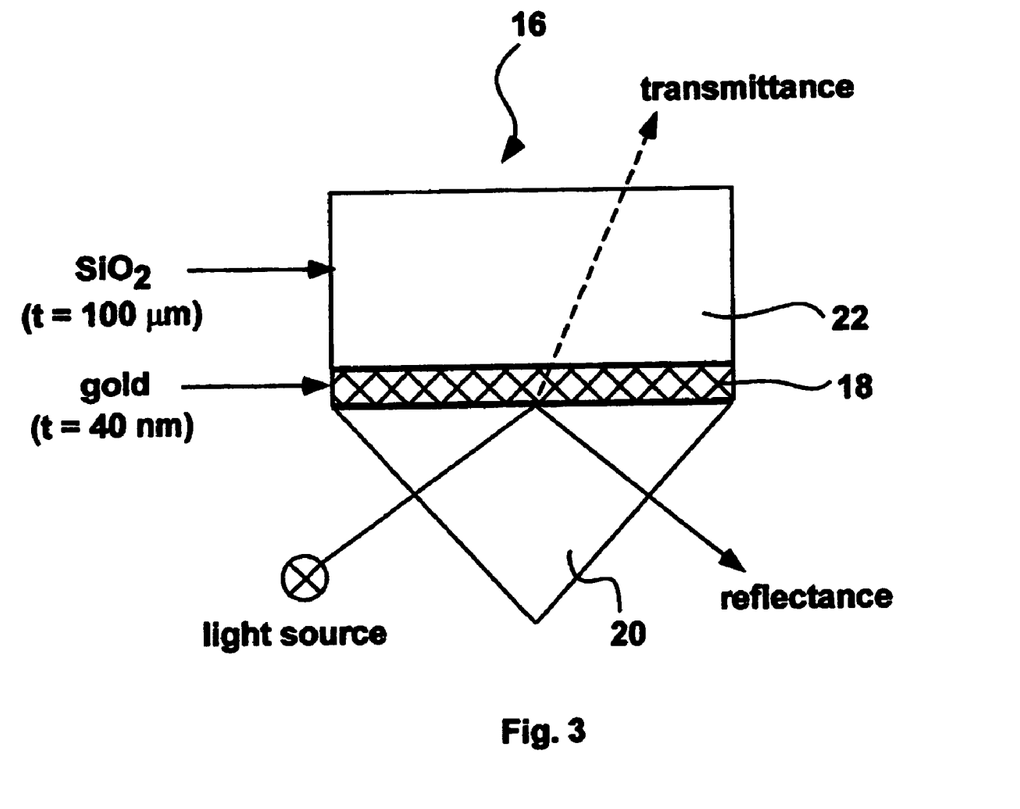
FIG. 3 is a schematic view of a second preferred embodiment of the invention that includes a metal layer for generating coupled-plasmon effects.

Turning to FIG. 3, a preferred embodiment of the invention featuring a sensor device 16 that includes a metal (or semi-conductor) layer 18 or layers with suitable optical parameters and thickness (e.g., gold or silver between 25-85 nm in thickness) and in which surface plasmons can be generated by light is shown. The metal layer 18 is deposited either directly on an entrant medium 20 (i.e., either a prism or a diffraction grating) or on a very thin layer (e.g., on the order of a few nanometers thick) of some additional material (not shown) that is used to improve adhesion of the metal layer to the entrant medium surface.

The metal layer 18 is either coated with an emergent medium (dielectric member 22) or is in optical contact with it. The dielectric member 22 may include either one or many layers of different materials and is designed in this embodiment to function both as an optical waveguide and an optical interference system. Accordingly, the thickness of the dielectric material is on the order of micrometers in thickness, typically between 10-1000 microns. Thus, one of the main advantages of this embodiment of the invention is its high sensitivity and spectral resolution in characterizing the optical properties of small amounts of materials immobilized on surfaces and interfaces for all incident angles of light between 0 and 90 degrees. Another advantage is that the sensor device of the invention uses thick and easily replaceable dielectric members made from a wide range of materials. Thus, high throughput sensor applications can be readily fabricated.

Figure 4A:
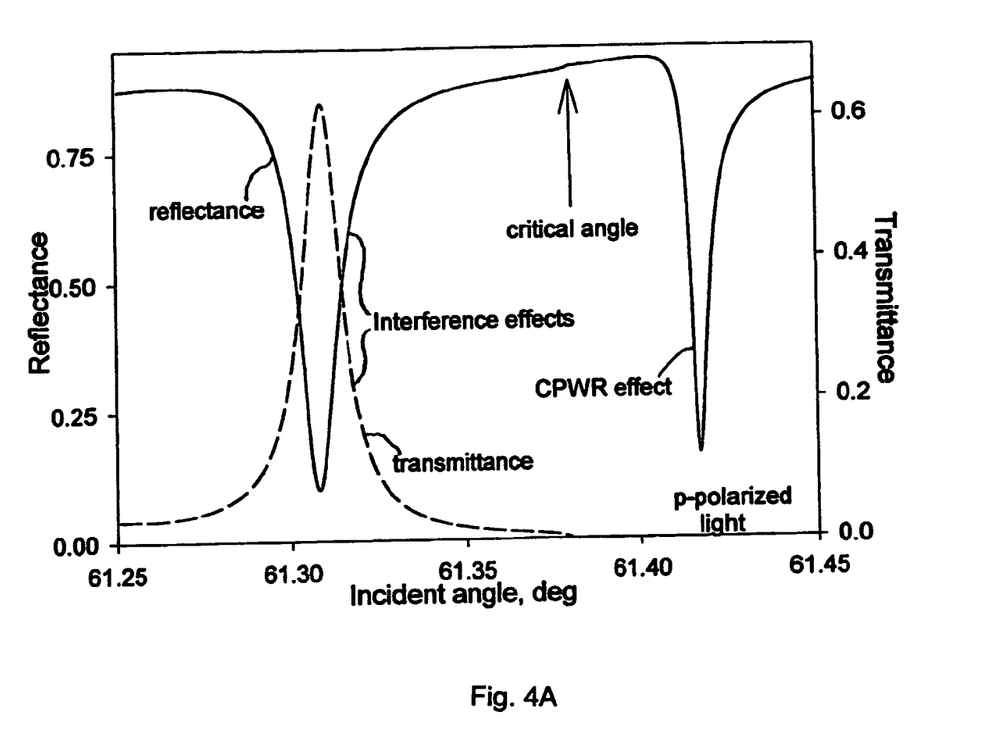
FIG. 4A illustrates spectra obtained with the sensor device of FIG. 3 in both transmittance and reflectance modes using p-polarized light.
Figure 4B:
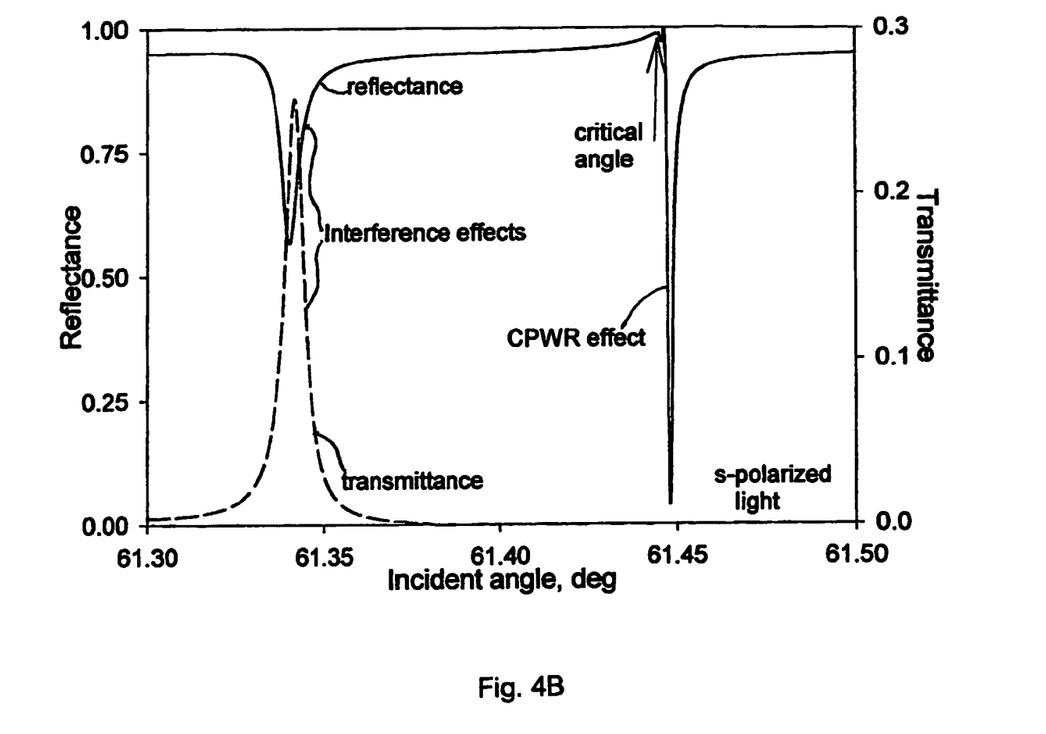
FIG. 4B illustrates spectra obtained with the sensor device of FIG. 3 in both transmittance and reflectance modes using and s-polarized light.

FIGS. 4A, B through 6A, B illustrate the plasmon resonance and interference spectra obtained from the device of FIG. 3, either with p- or s-polarized light as indicated in the brief description of the figures above. As can be seen from the data in these figures, and in contrast with previous sensor designs, the sensor device of the invention is able to generate p- and s-polarized observable effects both above (i.e., resonance effects) and below (i.e., interference effects) the critical angle and can measure interference effects using both reflectance and transmittance modes.

Figure 5A:
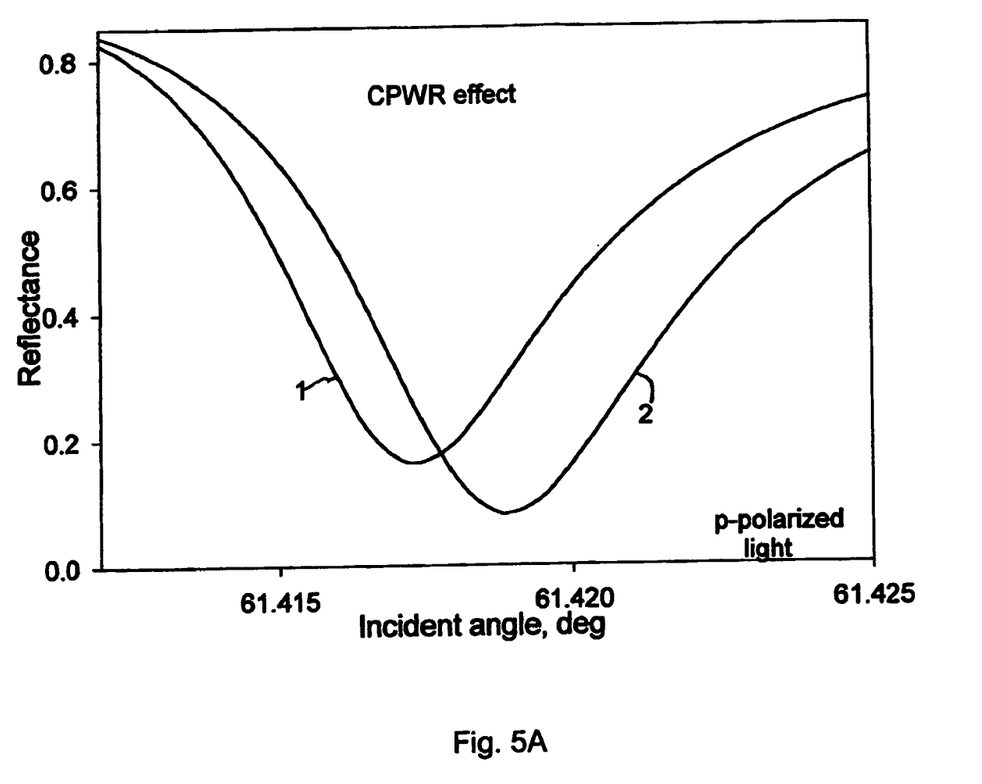
FIG. 5A illustrates the reflectance spectra measured above the critical angle for total internal reflection (see FIGS. 4A, B) using p-polarized light. Curve 1 shows the spectrum obtained with a bare sensor in contact with an aqueous solution (as shown in FIG. 3), whereas curve 2 represents the spectrum of the sensor with an additional coating that has the same optical properties as a typical lipid bilayer membrane.
Figure 5B:
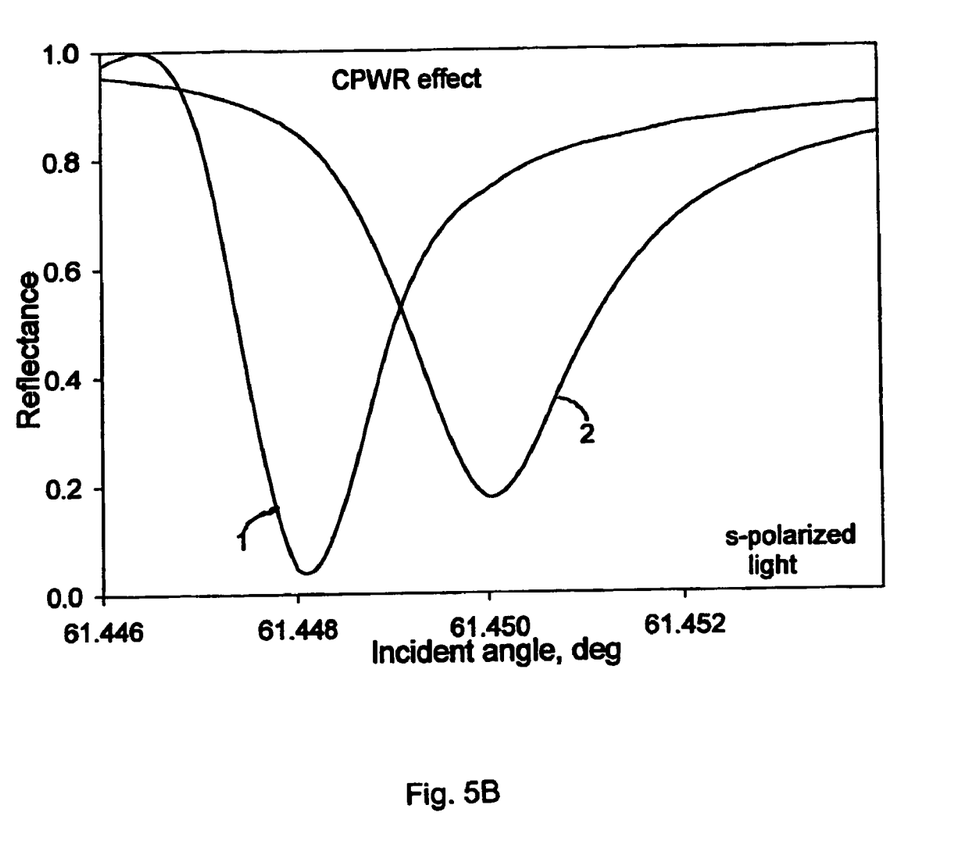
FIG. 5B illustrates the reflectance spectra measured above the critical angle for 20 total internal reflection (see FIGS. 4A, B) using s-polarized light. Curve 1 shows the spectrum obtained with a bare sensor in contact with an aqueous solution (as shown in FIG. 3), whereas curve 2 represents the spectrum of the sensor with an additional coating that has the same optical properties as a typical lipid bilayer membrane.
Figure 6A:
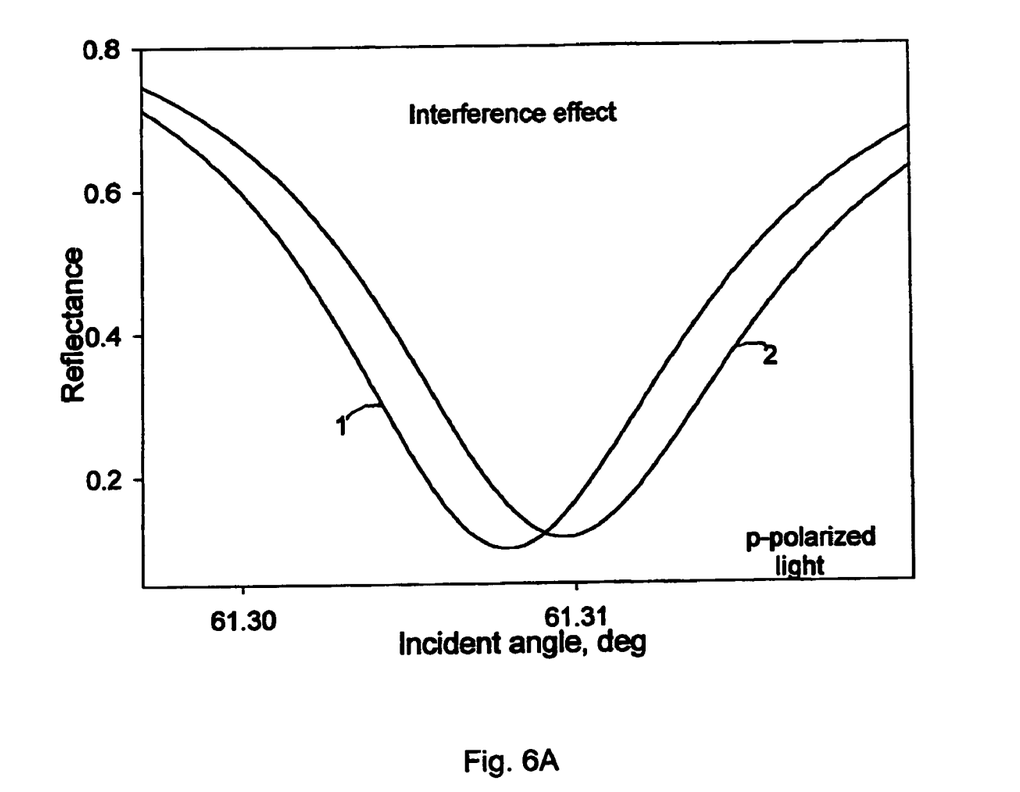
FIG. 6A illustrates reflectance spectra measured below the critical angle obtained with the sensor device of FIG. 3 using p-polarized light. Curves 1 and 2 are as described in the legend for FIGS. 5A, B.
Figure 6B:
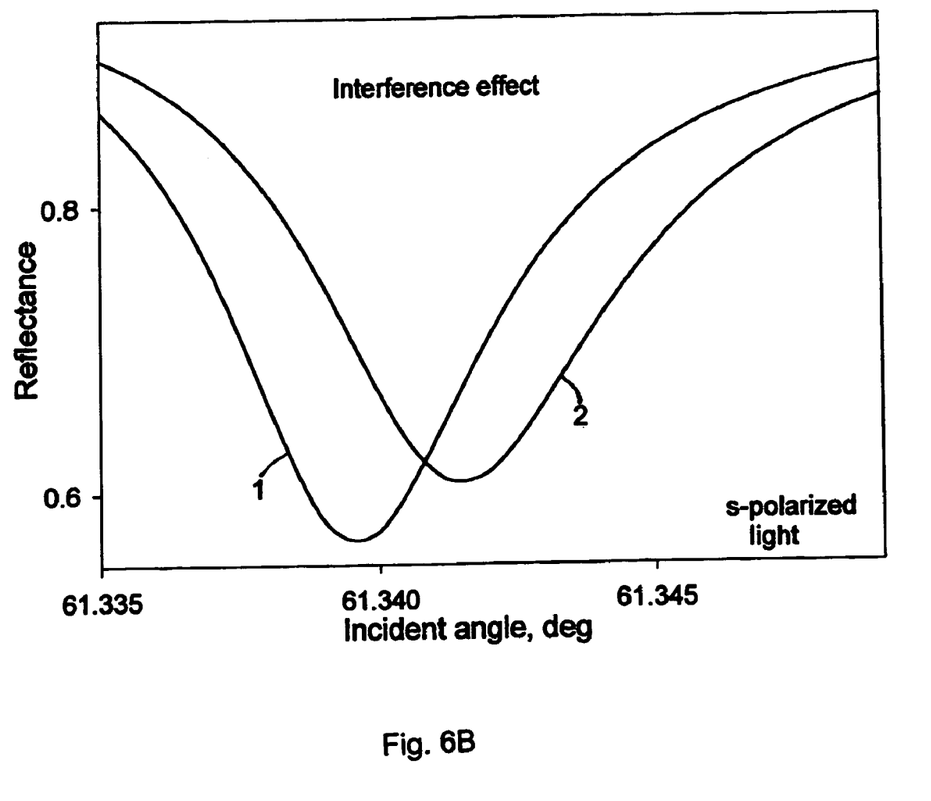
FIG. 6B illustrates reflectance spectra measured below the critical angle obtained with the sensor device of FIG. 3 using s-polarized light. Curves 1 and 2 are as described in the legend for FIGS. 5A, B.
Figure 7A:
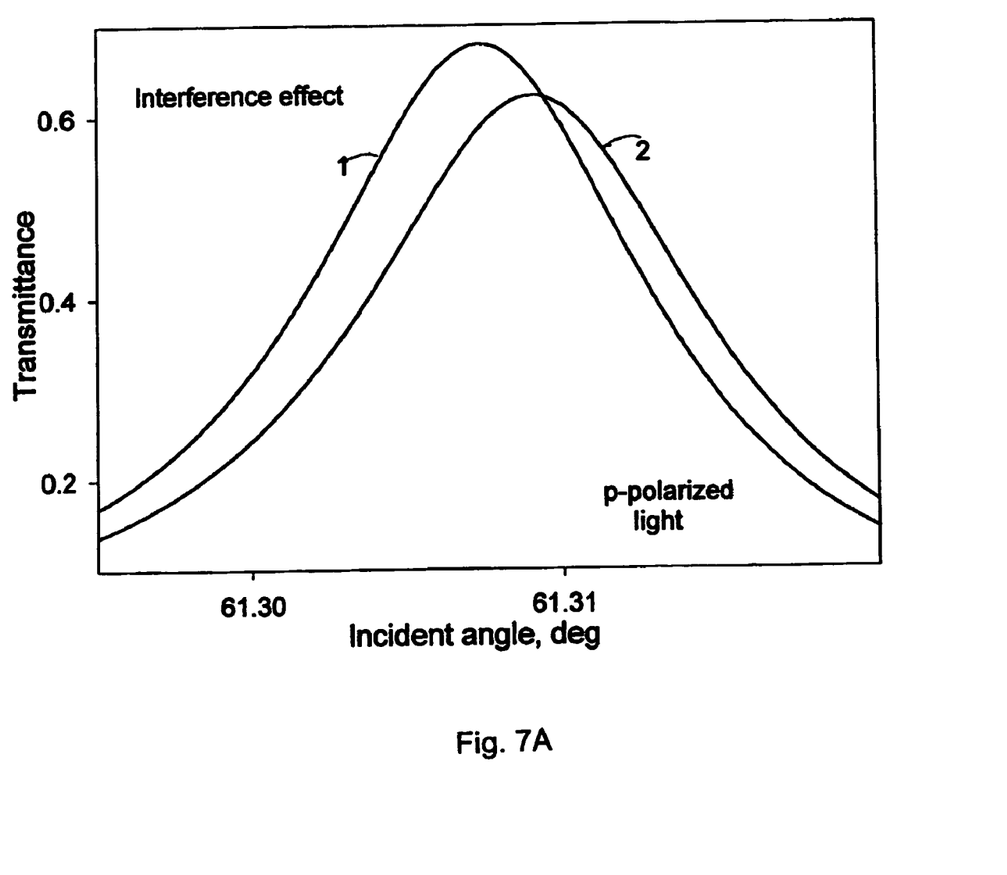
FIG. 7A illustrates transmittance spectra obtained using p-polarized light as described in the legend for FIG. 6A.
Figure 7B:
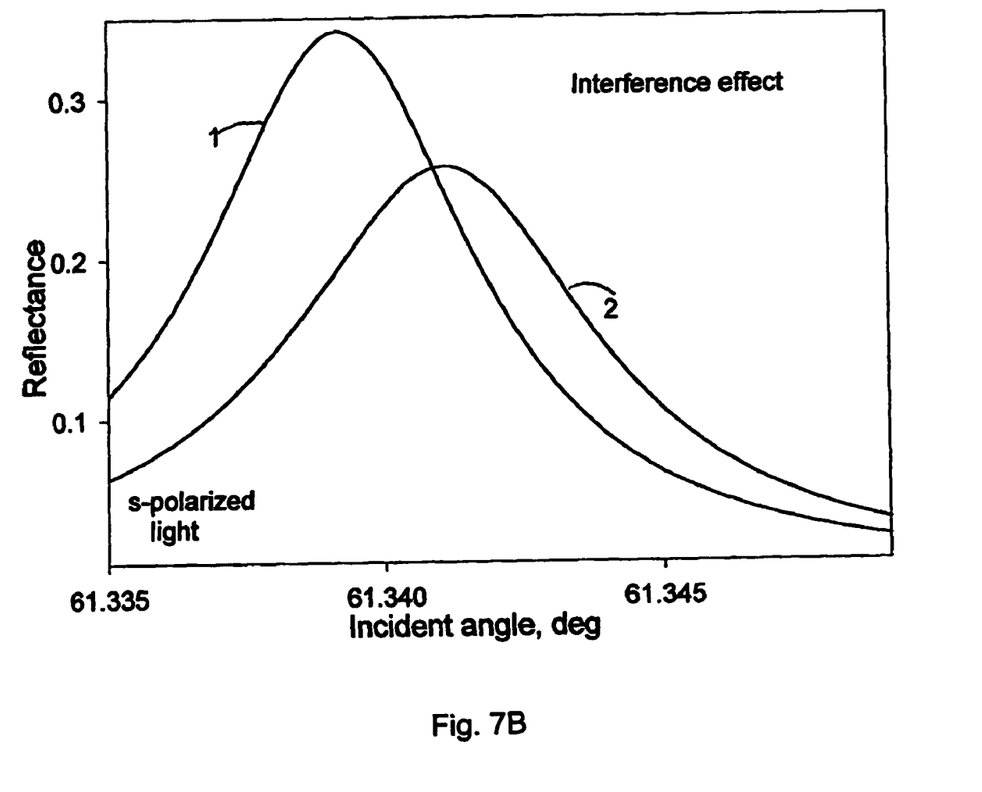
FIG. 7B illustrates transmittance spectra obtained using s-polarized light as described in the legend for FIG. 6B.

The device is highly sensitive to changes in the optical properties of the interface between the dielectric layer and the emergent medium. This can be demonstrated by comparing spectra obtained with and without an additional thin film coating. FIGS. 5A and 5B represent spectra measured above the critical angle with p- and s-polarized light, respectively, whereas FIGS. 6A and 6B represent reflectance and transmittance spectra measured below the critical angle. Curves 1 show the spectra obtained with a bare sensor in contact with an aqueous solution and curves 2 the sensor with an additional coating that has the same optical properties as a typical lipid bilayer membrane. FIGS. 7A (using p-polarized light) and 7B (using s-polarized light) show the transmittance spectra obtained as described for FIGS. 6A and 6B, respectively.

Choosing materials with the appropriate optical parameters and physical properties allows the device to be used in a large variety of applications. For example, the sensor of the invention can be used in a wide spectral range (from the ultraviolet to the infrared electromagnetic regions). Furthermore, the micrometer thickness of the dielectric layer allows different forms of surface modification of the senor chip to be used, including various types of lithographic and etching techniques to create specialty sensors. For example, minipore arrays within which lipid bilayers can be deposited for high throughput sensors can be created.

Furthermore, the thick dielectric film can also be designed to serve both as an optical and an electrical device that is capable of monitoring simultaneously electrical characteristics and optical parameters of thin films and interfaces. Also, the device of the invention can be used to characterize light-absorbing chromophores within different spectral ranges and at multiple wavelengths. Thus, the sensor of the invention can be used in all forms of surface plasmon resonance-based spectrometers and biosensors, as well as in all other optical and measurement techniques using surface phenomena.

A biosensor is generally defined as a unique combination of a receptor for molecular recognition, for example a selective layer with immobilized antibodies, and a transducer for transmitting the values measured. Accordingly, a biosensor will detect the change which is caused in the optical properties of a surface layer due to the interaction of the receptor with the surrounding medium (such as could be detected by SPR, CPWR, or PWI). Thus far, however, work on the development of biosensors has focused almost exclusively on various methods for binding a particular biomolecule to the metal surface of an SPR device. For example, in U.S. Pat. No. 5,492,840, Malmqvist et al. discloses a sensor unit for use in SPR-based systems that features a metal film having several sensing surfaces that have been disposed thereon and functionalized with antibodies and various other chemical elements.

Biomembranes, such as lipid bilayers, have been described and used to modify the dielectric member of a SPR and CPWR devices. While this type of surface modification would also allow the use of the present invention in biosensor applications, a great number of chemical or pharmaceutical samples will not be immobilized. Hence, functionalization of the dielectric layer found on the sensor of the invention provides the ability to perform interference-based or coupled-plasmon waveguide/interference spectroscopy (PWI) with wide variety of biological and non-biological molecules.

The functionalized sensors of the invention may be made in one piece, for example, from a glass slide (a dielectric material). Accordingly, in one embodiment of the invention, a layer of an organic polymer or a hydrogel forming a so-called basal surface that contains functional groups for binding the desired ligands is applied to the surface of the glass slide. These organic polymer or hydrogel layers thus become sensing surfaces.

For measurements to be carried out, the sensing surfaces have to be functionalized with different ligands capable of interaction with a target chemical or molecule. Several routes are available in achieving such functionalization. For example, the basal surface may be provided with a particular ligand during the manufacturing process or a user may provide his or her own. The ligands employed are bi- or polyfunctional, meaning that the ligands contain a function that is utilized for immobilization on a corresponding sensing surface of the dielectric layer, plus one or more bioselective functions for interaction with molecules in a sample.

So-called chimeric molecules (bi- or polyfunctional molecules) can be employed for functionalizing the sensing surfaces of the dielectric layer. The chimeric molecules comprise one portion binding to the basal surface, e.g., a dextran-coated sensing surface, and one portion having an affinity for the biomolecule to be detected. Bi- or polyfunctional molecules for use according to the invention may be produced in a variety of ways, e.g., by means of chemical coupling of the appropriate molecules or molecule fragments, by means of hybridoma techniques for producing bifunctional antibodies, or by means of recombinant DNA techniques. This last-mentioned technique involves the fusing of gene sequences coding for the structures which are wanted in the product, this product then being expressed in a suitable expression system such as, e.g., a culture of bacteria. The covalent immobilization of nucleic acids to the sensing surface can then be accomplished as described in Swanson, M. J. et al. "Reactive Polymer-Coated Surfaces for Covalent Immobilization of Nucleic Acids" (describing activated glass surfaces available from Amersham Biosciences as a "CodeLink Activated Slide" and formerly available from Surmodics, Inc. as a "3D-Link Microarray Slide.").

Chemical coupling of biomolecules or fragments thereof can be performed in accordance with one of the coupling methods that have been developed for the immobilization of biomolecules (see, for example, Moser, I. et al., Sensors and Actuators B. 7, (1992) 356-362). A suitable reagent is, e.g., SPDP N-succinimidyl 3-(2-pyridylthio)propionate, a heterobifunctional reagent (from Pharmacia AB, Sweden), and with a coupling technique as described by Carlsson et al. Biochem. J. 173:223 (1978). In the case of dextran, the chimeric molecule may consist of an antibody against dextran conjugated with a biospecific ligand, e.g., an immunoglobulin.

According to an alternative procedure, a sensing surface is modified with a so-called hapten for binding chimeric molecules to the surface. Thus, for example, a reactive ester surface as described above may be derivatized with a theophylline analog which is then utilized for binding chimeric molecules. In this case, the chimeric molecule consists of an antibody against theophylline conjugated with a biospecific ligand. This alternative embodiment very clearly reveals the great versatility attainable with the use of surfaces according to the present invention, inasmuch as it is very easy for the user to provide the same single basal surface with the desired ligand (e.g., receptor).

Proteins as a base for chimeric molecules (i.e., the surface binding structure thereof) must have strong bonds to their low-molecular chemically stable partners on the measuring basic surface. Also, no part thereof should, of course, be capable of interacting with the biosystems to be analyzed. Thus, in order to control non-specific binding, a biospecific pair derived from a plant, for example, could be used in the measurement of analytes containing human proteins.

Preferably, the analytical system is such that the binding of the chimeric molecule to the analyte may be reversed under conditions differing from those permitting the binding between the measuring surface and the chimeric molecule to be broken. In such manner, depending on the conditions, the sensing surface may be regenerated at two different levels, i.e., either for binding a new analyte, or for re-functionalizing the surface with the same or other chimeric molecules.

It is noted that the effects on the dielectric layer of the invention are not diminished by the addition of a very thin (1-5 nm) layer of gold (or other metal or a semiconducting material) at the interface with the emerging medium for the purpose of fixating the analyte to the sensing molecules. Such a combination of properties in one interface permits the construction of a durable sensor device with very high sensitivity and an expanded dynamic range of measurements. In other words, the addition of a very thin overcoating of the dielectric layer with a metal or semiconductor determines the type of chemistry required for surface modification and functionalization.

As is known to those skilled in the art, sulfur-bearing compounds can easily modify metal surfaces (including noble metal surfaces). Long-chain thiols, such as $HS(CH_2)_nX$ with n>10, adsorb from solution onto noble metals and form densely packed oriented monolayers (See, in general, S. Heyse et al. Biochimica et Biophysica Acta 85507 (1998)

319-338). The terminal group, X, of the thiol can be chosen from a wide variety of functional groups to interact properly with sample molecules. The choice of functional group determines the properties of such modified surfaces and its interaction with sample molecules. Monolayers of alkylthiols ($X=CH_3$) may serve as hydrophobic supports, allowing samples to be immobilized by hydrophobic interactions. Alternatively, hydroxythiols ($X=OH$) make the surface hydrophilic. Titratable terminal groups (e.g., $X=COO$ or $X=NH_3^+$) confer hydrophilicity and charge the surface, which varies as a function of pH. Some other examples are: amino, aldehyde, hydrazide, carbonyl or vinyl groups.

The reaction occurring when these or other groups are used for coupling various types of sample molecules are well known from the literature. More complex thiols can be used to serve special functions. For example, polyethylene-glycol-therminated thiols, biotyinylated thiols or thoalkanes bearing metal chelating groups allow the immobilization of histidine-tagged proteins and lipids to metal surfaces. More complex surfaces can easily be created by co-adsorbing two or more thiols with different functional groups.

Figure 8:
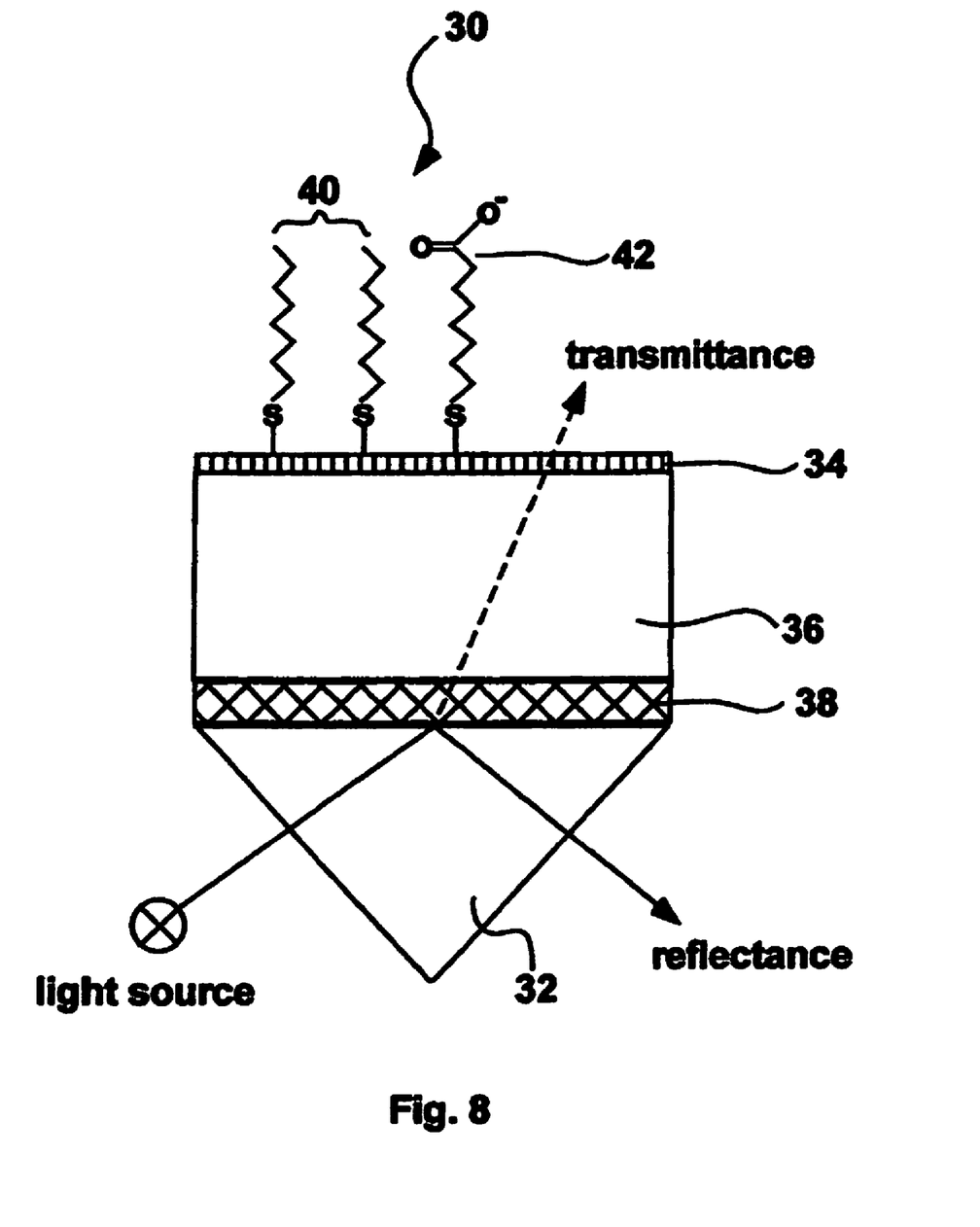
FIG. 8 is a schematic view of a third embodiment of the invention featuring dielectric surface functionalization.

Turning to an example of chemical surface modification, FIG. 8 depicts a PWI sensor 30 that includes a prism 32 upon which a layer of metal 34 is disposed. Below the metal layer 34 is a thick dielectric material 36, thus forming a basic PWI device. Additionally, disposed upon dielectric 36 is a very thin layer of metal 38 (e.g. gold). The layer of gold 38 has been chemically modified with molecules 40 and 42 (which are, in this case, molecules of tetradecanethiol and 11-mercaptoundecanoic acid, respectively). Molecules 40 may act as sensing molecules (for example, to bind a hydrophobic sample molecule, such as a phospholipid). Molecule 42 may provide a basal layer for further functionalization of sensor 30 (e.g., by binding a bi- or polyfunctional hydrophilic sensing molecules).

Employing an oxide as the dielectric layer conveys the advantage of intrinsic hydrophilicity. Thus, for certain applications (e.g., for self-assembled bilayer formation, see above) it need not be chemically modified. If functionalization is desired, silane chemistry, which is well known in the chemical literature, is the most appropriate approach (see, for example, Bhatia, Suresh K. Analytical Biochemistry (1989) 178, 408-413 (1989). Thus, antibodies can be immobilized on the dielectric $SiO_2$, for example. In principle, surface properties can be controlled using silane monolayers in the same way as with the thiol-metal chemistry described above.

The invention thus relates to a replaceable sensor unit which is to be used in systems based on many spectroscopy techniques. Each sensing surface contains at least one functional group, with sensor units for use in high-throughput screening having different functional groups or ligands for interaction with a plurality of molecules present in the sample to be analyzed. The invention moreover relates to processes for further functionalization of these sensing surfaces by binding to them bi- or polyfunctional ligands which will interact with molecules in the sample when the measuring operation is taking place.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and devices.

What is claimed is:

1. A spectroscopy system utilizing a light incident to an interface with a dielectric layer for measuring properties of molecules at surfaces and interfaces, comprising:
a plasmon waveguide sensor including an entrant medium and said dielectric layer, wherein said dielectric layer is of an optical thickness selected to produce an observable interference effect for an incident angle below a critical angle at an interface with the dielectric layer.

2. The system of claim 1, wherein said dielectric layer is between 10 and 1000 micrometers in thickness.

3. The system of claim 1, wherein said observable interference effect is measured both in transmittance and reflectance.

4. The system of claim 1, wherein the sensor further includes a metal or semiconductor layer disposed between said entrant medium and said dielectric layer.

5. The system of claim 1, wherein the sensor further includes a metal or semiconductor layer disposed at an interface with said dielectric layer.

6. The system of claim 1, wherein said sensor further includes at least one sensing area formed at an interface with an emergent medium, said at least one sensing area having undergone functionalization such that a target chemical within a sample material is immobilized.

7. The system of claim 6, wherein said at least one sensing area comprises a layer of an organic polymer and at least one functional group supporting bi- or polyfunctional sensing molecules.

8. The system of claim 7, wherein said at least one functional group is selected from the group consisting of hydroxyl, carboxyl, amino, aldehyde, hydrazide, carbonyl, and vinyl.

9. The system of claim 7, wherein said layer of an organic polymer comprises a polysaccharide.

10. The system of claim 7, wherein said functional group is selected from one or more members of the group consisting of ion exchanger groups, metal chelating groups, and receptors for biological molecules.

11. The system of claim 4, wherein said sensor further includes at least one sensing area formed at an interface with an emergent medium, said at least one sensing area having undergone functionalization such that a target chemical within a sample material is immobilized.

12. The system of claim 11, wherein said at least one sensing area comprises a layer of an organic polymer and at least one functional group supporting bi- or polyfunctional sensing molecules.

13. The system of claim 12, wherein said at least one functional group is selected from the group consisting of hydroxyl, carboxyl, amino, aldehyde, hydrazide, carbonyl, and vinyl.

14. The system of claim 12, wherein said layer of an organic polymer comprises a polysaccharide.

15. The system of claim 12, wherein said functional group is selected from one or more members of the group consisting of ion exchanger groups, metal chelating groups, and receptors for biological molecules.

16. In a coupled plasmon-waveguide resonance spectroscopic device, wherein a surface plasmon is excited by a light beam and propagated along a metallic or semiconductor film to measure a property of a sample material placed at an interface of an emergent medium, the improvement comprising a dielectric layer inserted between said film and said emergent medium, wherein said dielectric layer is of an optical thickness selected to produce an observable interference effect for an incident angle of light below a critical angle at an interface with the dielectric layer.

17. The device of claim 16, wherein said dielectric layer is between 10 and 1000 micrometers in thickness.

18. The device of claim 16, wherein said observable interference effect is measured both in transmittance and reflectance.

19. The device of claim 16, further including at least one sensing area formed at said interface with the emergent medium, said at least one sensing area having undergone functionalization such that a target chemical within said sample material is immobilized.

20. The device of claim 19, wherein said at least one sensing area comprises a layer of an organic polymer and at least one functional group supporting bi- or polyfunctional sensing molecules.

21. The device of claim 20, wherein said at least one functional group is selected from the group consisting of hydroxyl, carboxyl, amino, aldehyde, hydrazide, carbonyl, and vinyl.

22. The device of claim 20, wherein said layer of an organic polymer comprises a polysaccharide.

23. The sensor of claim 20, wherein said functional group is selected from one or more members of the group consisting of ion exchanger groups, metal chelating groups, and receptors for biological molecules.

24. A method for measuring a property of a sample material present at an interface of an emerging medium in a spectroscopic device that includes an interface with a dielectric member, comprising the following steps:
   (a) selecting the dielectric member with an optical thickness capable of producing an observable interference effect within the dielectric member for an incident angle of light below a critical angle of total internal reflection at said interface with the dielectric member;
   (b) placing said sample material at said interface of the emerging medium of the spectroscopic device; and
   (c) performing spectroscopic measurements with light having an incident angle below said critical angle of total internal reflection.

25. The method of claim 24, wherein said dielectric member of steps (a) and (b) is between 10 and 1000 micrometers in thickness.

26. The method of claim 24, wherein said observable interference effect is measured both in transmittance and reflectance.

27. A method for measuring a property of a sample material present at an interface of an emerging medium in a surface-plasmon spectroscopic device, wherein a surface plasmon is excited by a light beam and propagated along a metallic or semiconductor film, comprising the following steps:
   (a) coating said film with a dielectric layer being of an optical thickness selected to produce an observable interference effect within the dielectric member for an incident angle of light below a critical angle of total internal reflection at an interface with said dielectric layer;
   (b) placing said sample material at said interface of the emerging medium of the surface-plasmon-resonance spectroscopic device; and
   (c) performing spectroscopic measurements with light having an incident angle between 0 and 90 degrees.

28. The method of claim 27, wherein said dielectric member of steps (a) and (b) is between 10 and 1000 micrometers in thickness.

* * * * *